United States Patent [19]

Ullman et al.

[11] 4,039,385

[45] Aug. 2, 1977

[54] CARDIAC GLYCOSIDE ENZYME CONJUGATES

[75] Inventors: Edwin F. Ullman, Atherton; Kenneth E. Rubenstein, Menlo Park, both of Calif.

[73] Assignee: Syva Company, Palo Alto, Calif.

[21] Appl. No.: 649,942

[22] Filed: Jan. 19, 1976

Related U.S. Application Data

[60] Continuation-in-part of Ser. No. 481,022, June 20, 1974, abandoned, which is a division of Ser. No. 304,157, Nov. 6, 1972, Pat. No. 3,852,157, which is a continuation-in-part of Ser. No. 143,609, May 14, 1971, abandoned.

[30] Foreign Application Priority Data

| May 15, 1972 | United Kingdom | 22778/72 |
|---|---|---|
| May 10, 1972 | Canada | 141803 |
| May 12, 1972 | France | 72.17130 |
| May 12, 1972 | Switzerland | 7097/70 |
| May 8, 1972 | Sweden | 6049/72 |
| May 12, 1972 | Germany | 2223385 |

[51] Int. Cl.$^2$ ............................................. C07G 7/02
[52] U.S. Cl. ................................. 195/63; 195/103.5 R
[58] Field of Search ........................... 195/63, 103.5 R

[56] References Cited

U.S. PATENT DOCUMENTS

| 3,654,090 | 4/1972 | Schuurs et al. | 195/103.5 R |
|---|---|---|---|
| 3,850,752 | 11/1974 | Schuurs et al. | 195/63 |

OTHER PUBLICATIONS

Medical Pharmacology 7th Edition, p. 381 (1974).

*Primary Examiner*—Alvin E. Tanenholtz
*Attorney, Agent, or Firm*—Townsend and Townsend

[57] ABSTRACT

Enzyme conjugates are prepared of cardiac glycosides and aglycones for use in homogeneous enzyme immunoassays. The conjugates retain a substantial degree of the original activity of the enzyme and upon binding of receptor to the steroid moiety, a substantial diminution of enzyme activity is obtained. Various linking groups are employed for linking the steroid portion of the molecule to the enzyme, such as non-oxo carbonyl groups.

13 Claims, No Drawings

CARDIAC GLYCOSIDE ENZYME CONJUGATES

CROSS-REFERENCE RELATED APPLICATIONS

This application is a continuation-in-part of application Ser. No. 481,022, filed June 20, 1974, now abandoned which in turn is a division of application Ser. No. 304,157, filed Nov. 6, 1972, now U.S. Pat. No. 3,852,157, which in turn was a continuation-in-part of application Ser. No. 143,609, filed May 14, 1971, now abandoned.

BACKGROUND OF THE INVENTION

1. Field of the Invention

Because of the wide use of drugs derived from digitalis in the treatment of the cardiac patients and its substantial side effects, it is important to monitor the level of these drugs in the bloodstream of the patient. Digitalis is a complex mixture which includes digoxin and digitoxin which are the glycosides of digoxigenin and digitoxigenin.

A satisfactory method for assay for the active components of digitalis should be sensitive to the low concentrations of the components which will be present in blood serum. In addition, the assay should be highly specific for the materials of interest, so as to accurately reflect the presence of those materials and not other materials of similar structure. That is, there should be a minimal amount of cross reactivity in order to preclude false positive results. Desirably, the assay should require only small samples, should be rapid, should require a minimum number of manual steps, and should be useable on generally available equipment. Other desiderata include ease of handling of the reagents, stability of the reagents during storage and use, freedom from interference from naturally occurring contaminants, and being reasonably safe in handling.

2. Description of the Prior Art

See the references cited in the parent application, now U.S. Pat. No. 3,817,837, which is incorporated herein by reference. See also U.S. Pat. Nos. 3,791,932, 3,839,153 and 3,850,752.

SUMMARY OF THE INVENTION

Enzyme conjugates of cardiac glycosides and aglycones are provided. These conjugates, refered to as enzyme-bound-ligands where the ligand is the cardiac glycoside or aglycone, are prepared by modifying the cardiac glycoside or aglycone to introduce a functionality which can be used to form covalent bonds, particularly amide bonds, to the enzyme. The resulting enzyme-bound-ligand retains a substantial proportion of the orginal enzyme activity and upon binding of receptor for the ligand to the enzyme-bound-ligand, a substantial diminution in enzyme activity is observed. The enzyme-bound-ligands find use in homogeneous enzyme immunoassays for the detection of low concentrations of the cardiac glycosides and aglycones in physiological fluids e.g. serum.

DESCRIPTION OF THE SPECIFIC EMBODIMENTS

The subject invention concerns compositions for use in the determination of cardiac glycosides and aglycones which are enzyme-bound-ligands, where the ligand is a cardiac glycoside or aglycone and is modified so as to provide a functionality which can form a covalent bond to available functionalities on the enzyme, particularly amino and hydroxyl. The enzyme-bound-ligands find particular use in homogeneous enzyme immunoassays as described in U.S. Pat. No. 3,817,837. For the most part, the enzyme-bound-ligands of this invention will have the following formula

[Chemical structure showing a steroid-like framework with (HO)$_q$, OH, =O groups, labeled with $W^{a3}$, $A^*$, $n$, and "0-1 site of ethylenic unsaturation"]

wherein:

$n$ is on the average in the range of from about 1 to 20, more usually 2 to 16, and preferably of from about 2 to 10;

$q$ is 0 or 1;

$A^*$ is an enzyme, preferably an oxidoreductase, and particularly preferred a dehydrogenase; and $W^{a3}$ is a linking group which may be singly or doubly bonded to the annular carbon atom to which $W^{a3}$ is attached.

For the most part, the compounds will have one site of ethylenic unsaturation in the E ring, particularly in the alpha, beta position.

The nature of the linking group will vary, depending on whether the glycoside is involved or the aglycone.

Where the glycoside is involved, preferentially the terminal sugar will be cleaved to a dialdehyde, which may be conjugated directly to the enzyme by reductive amination or the dialdehyde may be derivatized to provide a carboxylic acid group, for example, with glycine, and the carboxy functionality employed to provide the covalent bond with the enzyme.

For the most part, the linking group $W^{a3}$ when involving a glycoside will have the following formula

[Chemical structure showing $CH_2Y$, $Y^1$, $Y^2$, $Y$, and O—(sugar-O)$_m$]

wherein:

sugar intends a sugar residue, usually a hexose, derived from L-rhamnose, L-cymarose, L-glucose, L-digitalose, L-digitoxose, and the like, wherein 1 or more of the hydroxyl groups may be acetylated;

$m$ will normally be from 0 to 2, usually being 2 when the sugar is digitoxose and being 0 when the sugar is other than digitoxose;

Y is hydrogen or hydroxyl, usually being hydrogen; and $Y^1$ and $Y^2$ are single bonds to amino residues of the enzyme or may be taken together together to provide an iminoalkylene(non-oxo-carbonyl) of from 2 to 8, more usually of from 2 to 6 carbon atoms and preferably of from 2 to 4 carbon atoms e.g. iminomethylene(non-oxo-carbonyl). Preferably, the sugar will be digitoxose and $Y^1$ and $Y^2$ will be taken together to form an iminoalkylene(non-oxo-carbonyl) group.

When a glycosidic linkage is involved, the linking group will generally be of from 6 to 30, more usually of from 6 to 26 carbon atoms and have the appropriate number of hydroxyl functionalities, which may or may not be acetylated.

When the aglycone is employed, the linking group may be varied widely and will generally be of from 1 to 12 atoms other than hydrogen, more usually of from 1 to 10 atoms other than hydrogen and normally including from 1 to 5, more usually from 1 to 4 heteroatoms which are chalcogen (oxygen and sulfur) or nitrogen. The linking group will normally be aliphatic, and may be aliphatically saturated or unsaturated, usually having from 0 to 1 site of ethylenic unsaturation as the only aliphatic unsaturation. Chalcogen will be present as non-oxo-carbonyl or oxy e.g. bonded solely to carbon and hydrogen, particularly carbon, except as provided for below, and nitrogen will be bonded solely to carbon e.g., tertiary amino, with the proviso that when neutral e.g. amido, or when imino, nitrogen may be bonded to from 0 to 1 hydrogen atom or when present as oximino or hydroxylamino, singly bonded to oxygen.

For the most part, the linking group of the aglycone will have the following formula

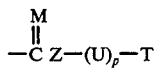

wherein:
T is a single or double bond to the annular carbon atom, being a single bond when bonded to oxygen, and a single or double bond when bonded to carbon or nitrogen;
p is 0 or 1;
U is amino (alkylamino of from 1 to 3 carbon atoms when T is a single bond), oxy, or aminooxy (derived from hydroxylamino i.e. oximino or hydroxylamino);
M is chalcogen or imino (=NH);
Z is aliphatic hydrocarbylene having from 0 to 1 site of ethylenic unsaturation as its only unsaturation and of from 1 to 7, more usually from 1 to 5 carbon atoms, preferably straight chained alkylene.

Illustrative linking groups include:
carbonylmethylene, carbonylmethoxy, carbonylbutylene-imino, carbonylpentyleneoxy, carbonylethyleneoximino, carbonylpropyleneoxyamino, imidoethyleneoxy and imidopropyleneoximino.

For the most part, the bonds to the enzyme will either be to amino groups, such as provided by lysine or terminal amino groups, to result in amide links or the nitrogen or thio analogs thereof (amidines or thioamides) or to hydroxyl groups, such as provided by typrosine or serine, to provide esters.

ENZYMES (A*)

Enzymes vary widely in their substrates, cofactors, specificity, ubiquitousness, stability to temperature, pH optimum, turnover rate, and the like. Other than inherent factors, there are also the practical considerations, that some enzymes have been characterized extensively, have accurate reproducible assays developed, and are commercially available. In addition, for the purposes of this invention, the enzymes should either be capable of specific labelling or allow for efficient substitution, so as to be useful in the subject assays. By specific labelling is intended selective labelling at a site in relationship to the active site of the enzyme, so that upon binding of the receptor to the ligand, the enzyme is satisfactorily inhibited. (By active site is intended those fuctionalities which are involved in the binding and transformation of the substrate(s) including cofactors). By allowing for sufficient substitution to be useful in the subject assay, it is intended that the enzyme be inhibited sufficiently when the ligand is bound to the receptor, and that the degree of substitution required to achieve this result does not unreasonably diminish the turnover rate for the enzyme, nor substantially change the enzyme's solubility characteristics.

From the standpoint of operability, a very wide variety of enzymes can be used. But, as a practical matter, there will be a number of groups of enzymes which are preferred. Employing the International Union of Biochemists (I.U.B.) classification, the oxidoreductases (1.) and the hydrolases (3.) will be of greatest interest, while the lyases (4.) will be of lesser interest. Of the oxidoreductases, the ones acting on the CHOH group, the aldehyde or keto group, or the $CH-NH_2$ group as donors (1.1, 1.2, and 1.4 respectively) and those acting on hydrogen peroxide as acceptor (1.11) will be preferred. Also, among the oxidoreductases as preferable will be those which employ nicotinamide adenine dinucleotide, or its phosphate or cytochrome as an acceptor, namely $1.\times.1$ and $1.\times.2$, respectively under the I.U.B. classification. Of the hydrolases, of particular interest are those acting on glycosyl compounds, particularly glycoside hydrolases, and those acting on ester bonds, both organic and inorganic esters, namely the 3.1 and 3.2 groups respectively, under the I.U.B. classification. Other groups of enzymes which might find use are the transferases, the lyases, the isomerases, and the ligases.

In choosing an enzyme for commercialization, as compared to single or limited use for scientific investigation, there will be a number of desirable criteria. These criteria will be considered below.

The enzyme should be stable when stored for a period of a least three months, and preferably at least 6 months at temperatures which are convenient to store in the laboratory, normally $-20°$ C or above.

The enzyme should have a satisfactory turnover rate at or near the pH optimum for binding to the antibody, this is normally at about pH 6-10, usually 6.0 to 8.0. Preferably, the enzyme will have the pH optimum for the turnover rate at or near the pH optimum for binding of the anitbody to the ligand.

A product should be either formed or destroyed as a result of the enzyme reaction which absorbs light in the ultraviolet region or the visible region, that is in the range of about 250-750 nm, preferably 300-600 nm.

Preferably, the enzyme should have a substrate (including cofactors) which has a molecular weight in excess of 300, preferably in excess of 500, there being no upper limit. The substrate may either be the natural substrate, or a synthetically available substrate.

Preferably, the enzyme which is employed or other enzymes, with like activity, will not be present in the fluid to be measured, or can be easily removed or deactivated prior to the addition of the assay reagents. Also, one would want that there not be naturally occurring inhibitors for the enzyme present in fluids to be assayed.

Also, although enzymes of up to 600,000 molecular weight can be employed, usually relatively low molecular weight enzymes will be employed of from 10,000 to 300,000 molecular weight, more usually from about 10,000 to 150,000 molecular weight, and frequently from 10,000 to 100,000 molecular weight. Where an enzyme has a plurality of subunits the molecular weight limitations refer to the enzyme and not to the subunits.

For synthetic convenience, it is preferable that there be a reasonable number of groups to which the ligand may be bonded, particularly amino groups. However, other groups to which the ligand may be bonded include hydroxyl groups, thiols, and activated aromatic rings, e.g. phenolic.

Therefore, enzymes will preferably be chosen which are sufficiently characterized so as to assure the availability of sites for linking, either in positions which allow for inhibition of the enzyme when the ligand is bound to antibody, or there exist a sufficient number of positions as to make this occurrence likely.

Of the various enzymes, the following table indicates enzymes of particular interest set forth in accordance with the I.U.B. classification.

1. Oxidoreductases
    1.1 Acting on the CH–OH group of donors
        1.1.1 With NAD or NADP as acceptor
            1. alcohol dehydrogenase
            6. glycerol dehydrogenase
            26. glyoxylate reductase
            27. L-lactate dehydrogenase
            37. malate dehydrogenase
            49. glucose 6-phosphate dehydrogenase
            17. mannitol 1-phosphate dehydrogenase
        1.1.2 With cytochrome as an acceptor
            3. L-lactate dehydrogenase
        1.1.3 With $O_2$ as acceptor,
            3. glucose oxidase
            9. galactose oxidase
    1.2 Acting on the CH–$NH_2$ group of donors
        1.43 With $O_2$ as acceptor
            2. L-amino acid oxidase
            3. D-amino acid oxidase
    1.6 Acting on reduced NAD or NADP as donor
        1.6.99 With other acceptors diaphorase
    1.10 Acting on diphenols and related substances as donors
        1.10.3 With $O_2$ as acceptor
            1. polyphenol oxidase
            3. ascorbate oxidase
    1.11 Acting on $H_2O_2$ as acceptor
        1.11.1
            6. catalase
            7. peroxidase
3. Hydrolases
    3.1 Acting on ester bonds
        3.1.1 Carboxylic ester hydrolases
            7. cholinesterase
        3.1.3 Phosphoric monoester hydrolases
            1. alkaline phosphatase
        3.1.4 Phosphoric diester hydrolases
            3. phospholipase C
    3.2 Acting on glycosyl compounds
        3.2.1 Glycoside hydrolases
            1 a-amylase
            4. cellulase
            17. lysozyme
            23. β-galactosidase
            27. amyloglucosidase
            31. β-glucuronidase
    3.4 Acting on peptide bonds
        3.4.2 Peptidyl-amino acid hydrolase
            1. carboxypeptidase A
        3.4.4 Peptidyl-peptide hydrolase
            5. α-chymotrypsin
            10. papain
    3.5 Acting on C-N bonds other than peptide bonds
        3.5.1 In linear amides
            5. urease
    3.6 Acting on acid anhydride bonds
        3.6.1 In phosphoryl-containing anhydrides
            1. Inorganic pyrophosphatase Lyases
    4.1 Carbon-carbon lyases
        4.1.2 Adldehyde lyases
            7. aldolase
    4.2 Carbon-oxygen lyases
        4.2.1 Hydrolases
            1. carbonic anhydrase
    4.3 Carbon-nitrogen lyases
        4.3.1 Ammonia lyases
            3. histidase The number of ligands which may be bonded to the enzyme will be limited by the number of available sites for bonding to the enzymes. In most cases, this will be the amino groups which are present, but as already indicated, carboxyl, hydroxyl, thiol and activated aromatic rings, e.g. phenolic, are also useful sites.

Various factors will affect the number of ligands which is optimum for a specific enzyme and a specific ligand. Of prime consideration is the number required for obtaining the desired degree of inactivation when receptor is bound to the enzyme-bound-ligand. The number required will vary with the mode of attachment and the conditions for attachment of the ligand to the enzyme. Except under special circumstances, e.g. affinity labeling, there will usually be differences in degree of inhibition, as to each site to which the receptor is bound to the enzyme through a ligand. In addition, there may be cumulative effects, with an increase in the number of receptors bound to the enzyme through ligand.

Other considerations as to the number of ligands per enzyme will be the effect of the increasing number of ligands on: solubility of the enzyme-bound-ligand; activity of the enzyme-bound-ligand in the absence of receptor; and the sensitivity of the assay. Therefore, the choice of the number of ligands bonded to the enzyme is usually empirically determined, based on the effect of varying the number of ligands on the enzyme has on the assay.

With small enzymes, e.g., lysozyme, those have molecular weights in the range of 10,000 to 30,000 from 2 to 10 ligands can be sufficient. With larger enzymes, e.g., malate dehydrogenase, of molecular weight in the range of 30,000 to 150,000, 2 to 30 ligands can be sufficient. For malate dehydrogenase 2 to 22 ligands on the average will be employed. As few ligands as possible should be bonded to the enzyme to achieve the desired degree of inhibition. Desireably, the number of ligands per enzyme should be in the range of 1 to 20, more preferably 1 to 112.

As already indicated, because of the diversity of enzymes which can be used for the assay and the variety of functionalities in the enzyme available for attachment, and the varying activities of the functionalities for being bonded to the ligand as well as their relative position to the active site of the enzymes, different numbers of ligands will be necessary for obtaining the desired degree of inhibition, when the enzyme-bound-ligand is bonded to antibody. Furthermore, the desired degree of inhibition may vary, depending on the sensitivity required for an assay for a particular ligand.

It is found, for the most part, that increasing the average number of ligands increases the amount of inhibition, up to a degree of substitution, where further substitution does not provide a significant increase in inhibition. Therefore, by varying the conditions for the reaction between the modified ligand (ligand and linking group) and the enzyme, varying degrees of substitution can be achieved. The time for the reaction, the mole ratio of ligand to enzyme and the like can be varied. Also, the reactive functionality on the linking group can be varied to change the number and sites for substitution. One can then empirically determine the number of ligands required for the desired degree of inhibition.

It should also be noted that in referring to inhibition of an enzyme, the substrate for the enzyme plays a role. Different degrees of inhibition may be achieved with different substrates. Thus, not only can one obtain varying degrees of inhibition by varying the number of ligands bonded to the enzyme, and the sites to which the ligands are bonded, but also, with some enzymes, by varying the substrate for the enzyme.

It is also found that with increasing substitution of the enzyme by ligand, there can be reduction in enzyme activity. The turnover number diminishes and there is a concomitant increase in the Michaelis constant. The decrease in turnover number with increasing substitution will vary with the enzyme. By employing enzymes which have a high initial activity, a loss of as much as 75% of initial activity can be tolerated.

(Turnover number is the number of substrate molecules transformed per unit time per enzyme molecule. Lehninger, Biochemistry, Worth Publisher, New York, 1970.) Since the turnover number is reported at varying temperatures and on varying bases, e.g., weight of protein as an indication of number of enzymes or change in a spectrophotometric value as as indication of number of substrate molecules, there is at the present no simple comparison between the turnover number of different enzymes. Therefore, no minimum numerical turnover number for preferred enzymes can be given.)

Also, the ligand will be attached to the enzyme by a relatively short chain, usually of the order of 1.5 to about 20A, more usually about 3 to 10A.

For the most part, at least about 20% of the original activity of the enzyme will be retained, preferably at least 40%, and more preferably at least about 50%. Inhibitability should be at least about 20%, preferably at least about 30%, and more preferably at least about 50%.

ENZYME ASSAY

Turning now to a consideration of the determination of the amount of active enzyme, assaying for enzymatic activity is well established for a wide variety of enzymes. A wide diversity of media, conditions and substrates have been determined for measuring enzymatic activity. See, for example, Bergmeyer, Methods for Enzymatic Analysis, Academic Press, New York, 1965. Since there are differences, not only between assays for different enzymes, but even in the variety of assays for a particular enzyme, no general description of the assay techniques can be given.

In the assay, antibodies for the appropriate cardiac glycoside or aglycone will be employed. These antibodies can be obtained by conjugation of the derivative of the cardiac glycoside or aglycone, the same or different derivative from the derivative employed for conjugation to the enzyme, and the antigenic conjugate injected into a vertebrate, particularly a domestic animal, in accordance with known techniques. Blood can then be removed from the animal and the antibodies isolated and purified as desired.

EXPERIMENTAL

The following examples are offered by way of illustration and not by way of limitation.

All temperatures are recorded in centigrade. All parts not otherwise indicated are by weight. All pressures not otherwise indicated are millimeters mercury (mm Hg).

EXAMPLE 1.

Preparation of 3-ketodigoxigenin from digoxigenen

A suspension of $PtO_2$ (44mg), in 12 ml of distilled water (twice distilled) was stirred under a hydrogen atmosphere at room temperature for 1 hr. The hydrogen was expelled using an aspirator and the flask repeatedly flushed with nitrogen. The flask was then disconnected from the hydrogenation apparatus and 10ml of distilled water was added to rinse down the catalyst adhering to the sides. After stirring the mixture for 15 minutes in an oxygen atmosphere, a solution of digoxigenin (400mg, mp. 205°–210°) in acetone (60ml) (distilled from potassium permanganate) and water (22ml, twice distilled) was added to the reaction flask. The reaction mixture was then stirred under an oxygen atmosphere at 22° for 24 hours. The catalyst was then filtered off the filtrate concentrated, and concentrated solution extracted with chloroform and dried over anhydrous sodium sulfate. Evaporation of solvent gave a crude product (475mg) which was recrystallized from acetone-ether to give 239mg, white solid (mp. 247°–251°, reported mp. 247°–252°).

EXAMPLE 2.

O-Carboxymethyl oxime of 3-ketodigoxigenin

A clear solution of 3-ketodigoxigenin (228mg, 0.59 mmoles), carboxymethoxylamine hydrochloride (140mg, 0.64 mmole) and sodium acetate (294mg, 3.6 mmole) in methanol (18ml, dried over molecular sieves 3A) was refluxed under nitrogen for 3 hours. The tlc of an aliquot showed the complete formation of oxime derivative ($R_f$ 0.33; 0.5:1:10/HOAc-MeOH-CHCl$_3$, Silica gel plate). The resulting reaction product was stripped to dryness, the residue dissolved in 32 ml 5% $NaHCO_3$ at 5°–10°, and extracted with 3×20ml chloroform. The bicarbonate layer was acidified at 5°–10° with 28ml of 1N hydrochloric acid to pH 2–3 and extracted with 10×25ml ethyl acetate. The ethyl acetate extracts were washed with saturated sodium chloride and dried over anhydrous sodium sulfate. Evaporation of solvent gave a solid which was recrystallized from a mixture of methanol-ethyl acetate-hexane to yield a white solid (188mg, mp. 202°–220°(dec)).

EXAMPLE 3.

Conjugation of the O-carboxymethyl digoxigenin-3keto oxime to G-6-PDH

To a dry flask, fitted with serum stopper and drying tube was introduced 23.05mg (0.05mmole) of the oxime and 250μl of DMF (dried over 4 A molecular sieves) and 7.1μl (0.052mmole) of dry triethylamine added through the serum stopper with a syringe with stirring at room temperature. After cooling the mixture to −14°, 9.3μl (0.05mmole) of carbitol chloroformate was added below the surface of the solution and the mixture stirred for 30 minutes.

In a separate flask, to 2ml of glucose-6-phosphate dehydrogenase (G6PDH) at a concentration of about 1–2mg/ml in 0.055M tris buffer, pH 8.1 with stirring is added 20mg of glucose-6-phosphate disodium salt and 40mg NADH. (During the reaction aliquots are taken and the enzyme activity is determined by diluting a 5μl aliquot of the enzyme solution to 5ml, and taking a 50μl aliquot of the diluted enzyme solution and diluting with 1ml buffer and 50μl substrate, introducing the solution into a 1.5ml sample cup and employing a flow cell, reading the enzyme activity over a 60 second interval in a Gilford spectrophotometer.) The mixture is cooled to 0° and with stirring 1.08ml carbitol added slowly with a syringe below the surface of the solution. After standing for 30 minutes, any precipitate is removed by centrifuging for 4 minutes with a Brinkman centrifuge and isolating the supernatant. The supernatant is adjusted to a pH of about 9.0 with 1N NaOH. The enzyme activity is checked at this time.

To a stirring solution of the enzyme, 1μl aliquots of the mixed anhydride prepared above are added to the enzyme at a rate of about 1μl per minute. After the addition of 10μl of the mixed anhydride, the percent inhibition and the percent deactivation are determined. Percent inhibition is determined by employing approximately 5μl of full strength antidigoxin in the above assay. About 35–45μl of the mixed anhydride are added to obtain an inhibition of about 50% and a deactivation of about 36%. When the desired inhibition and deactivation are obtained, the enzyme conjugate is purified by dialysis against 0.055M tris-HCl buffer, pH 8.1 containing 0.05% $NaN_3$ and 0.005% Thimerosal.

Following the above described procedure, in a first reaction, an enzyme conjugate was obtained having 5 digoxins conjugated to the enzyme, which was 36% deactivated and was 64% inhibited, while in a second reaction sequence, an enzyme conjugate was obtained having 9.4 digoxins, which was 26% deactivated and 48% inhibited.

EXAMPLE 4.

Preparation of Digoxin Dialdehyde

Digoxin (1.5g, 1.92mmole) was dissolved in 15ml of dimethylformamide (DMF) in a 100ml round bottom flask with the aid of a magnetic stirrer. A solution of 835mg (3.9mmole) of sodium periodate in 17ml of $H_2O$ was added dropwise over 15 minutes at 0°. The resulting colorless clear solution became cloudy slowly. The reaction was followed by tlc (silica gel, 10% $MeOH/CHCl_3$). After four hours the reaction was completed. The reaction mixture was added to 20ml of ice water, and taken up in 200ml of ethyl acetate and washed with 3×50ml of $H_2O$ and sat. brine, dried ($MgSO_4$) and concentrated to give 1.15g of product. A second crop of 250mg was obtained by extraction of the aqueous washings in the same manner. Both crops contained small amounts of DMF. Crude yield 1.40g, 94%.

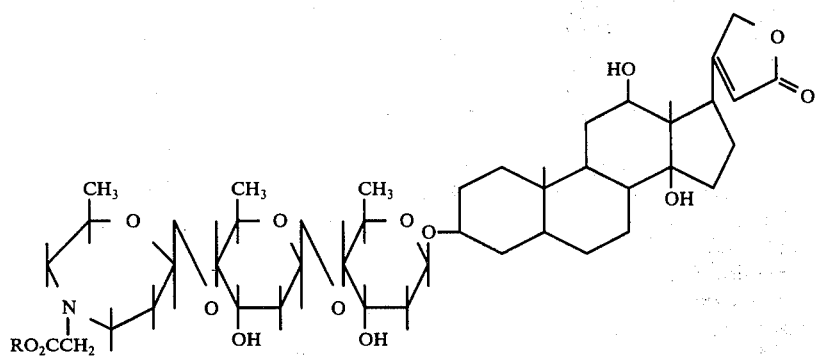

Example 5. R - benzyl
Example 6. R - H

EXAMPLE 5. R – benzyl

EXAMPLE 6. R – H

EXAMPLE 5.

Preparation of $O^4$-(N-carboxymethyl 2'methylhexahydro-1',4'-oxazepinyl-7') $O^{1''}$ -(3'''-digoxigeninyl-3'''-deoxy) O-β-D-digitoxpyranosyl(1→4)-O-β-D-digitoxpyranose benzyl ester To 312mg (0.4mmole) of digoxin dialdehyde (see prior example) dissolved in 10ml of dry MeOH at room temperature under an argon atmosphere was added a solution of glycine benzyl ester. Eighty-two mg (1mmole) of sodium acetate was added and the mixture was kept at pH 6.5 with MeOH-HCl solution and stirred for three hours. One hundred and thirty mg (2mmole) of $NaB(CN)H_3$ and another 123mg (1.5mmole) of sodium acetate was added. The mixture had a pH of ~7 and was stirred overnight.

To the reaction mixture was then added a few drops of HOAc and the mixture concentrated to dryness in vacuo to leave a solid residue. The residue was dissolved in 15ml of cold $H_2O$, extracted with 2×60ml of $CHCl_3$, washed with 2×20ml of $H_2O$, dried ($MgSO_4$), and concentrated to give 304mg of crude product. Preparative tlc on silica gel ($MeOH:CHCl_3$ = 1:9) gave 143mg of white solid (16% yield).

EXAMPLE 6.

Preparation of O⁴-(N-(carboxymethyl)hexahydro-1,4-(2-methyl)oxazepin-7-yl-)digoxigenin-didigitoxoside Fifty mg (0.055mmole) of the benzyl ester [see prior example] was dissolved in 25ml of absolute methanol. Then 25mg of Pd/C was added and the mixture was subjected to hydrogenation at atmospheric pressure and room temperature overnight. The resulting mixture was filtered through Celite, then concentrated to a glass which gave a white solid when scratched and treated with ether. Yield 35mg (78%).

EXAMPLE 7.

Preparation of G-6-PDH Conjugate with the Digoxigenin-didigitoxoside Derivative of Example 6

Following the procedure of Example 3, 53.1mg (0.05mmole) of the digoxigenin derivative of Example 6 was placed in a flask fitted with a serum stopper and drying tube and 250µl of dry DMF and 7.5µl of dry triethylamine added through the serum stopper with a syringe while stirring at room temperature. After cooling the flask to −14°, 9.3µl of carbitol chloroformate was added below the surface of the solution. The mixture was allowed to stir at −14° for 30 minutes.

The enzyme G6PDH was prepared as described in Example 3.

To the enzyme solution at 0° and at pH 9 was added 1µl aliquots of the mixed anhydride at a rate of 1µl per minute. Activity and inhibition checks were made after each 10µl of mixed anhydride had been added. Percent inhibition is determined by adding 5µl of full strength antidigoxin with the enzyme and substrate. Approximately 35–45µl of the mixed anhydride was added to yield an enzyme which after purification by dialysis against 0.055M tris-HCl buffer pH 8.1 (with 0.05% sodium azide and 0.005% Thimerosal), was 32% deactivated, had a maximum inhibition of 34% and a digoxin number of 13.4.

In order to demonstrate the efficacy of the subject composition in determining the presence of digoxin, a number of determinations were carried out. The following are the reagents employed and the protocol for the assay. Wherever W/V is employed, the intent is grams per 100ml.

Reagent A incorporates antibody and substrate for the enzyme glucose-6-phosphate dehydrogenase. The antibody employed was obtained by injection of the antigen prepared as described in Smith et al, Biochemistry, 9, 331 (1970). Specifically, the antibody was derived from sheep and was diluted 1:1000 and 18µl of the antibody solution employed. The bleed was the third bleed. The amount of antibody employed was sufficient to give 30% inhibition of the enzyme. The amount of enzyme employed provided a reading in the absence of antibody of 0.9 OD/30 minutes at 340nm at 30° C.

In reagent A in addition to the antibody, NAD is at 0.08M, G-6-P is at 0.13M, rabbit serum albumin is at 1% W/V and the system is buffered with tris-HCl, pH 7.9 (30° C), 0.055M, sodium azide at 0.05 W/V and Thimerosal at 0.005 W/V.

The second reagent, reagent B contains the enzyme at a concentration which upon final dilution in the assay provides a reading of 0.9 OD/30 minutes. In addition to the enzyme conjugate, prepared it accordance with Example 3, is rabbit serum albumin (RSA) 1% W/V, sodium chloride 0.9% W/V and buffer as described for reagent A.

In carrying out the assay, 200µl of serum is employed which is first treated with 50µl of 0.5N sodium hydroxide. The sodium hydroxide treatment aids in destroying background activity. The mixture is mixed by gentle tapping and allowed to incubate at 30° C for at least 15 minutes and not more than about 1 hour. After sufficient time, 50µl of reagent A is added with 700µl of buffer and the solution mixed and incubated for a period from 5 minutes to not more than about 1 hour. At the end of this time, reagent B is added with 700µl of buffer and a stopwatch begun at the moment of addition of reagent B. The mixture is agitated and then introduced into a spectrophotometer and a reading taken at 1 minute from the time of the addition of reagent B. The mixture is then allowed to sit in a thermostatted bath at 30° C for an additional 30 minutes and a second reading taken. The readings are reported in OD/min. and by employing appropriate standards, one can determine the concentration of the digoxin in amounts of as low as 0.5ng/ml.

Using serum samples spiked with known amounts of digoxin, a Δ OD × 1000 of 65.5 is obtained between a sample having 0.5ng/ml and 2.0ng/ml.

In replicates of a single serum pool, testing 30 specimens, a standard deviation of 0.07ng/ml was obtained with a coefficient of variation of 7.3% at 1.0ng/ml. Where 40 samples of different specimens were employed at a spiked value at 1.0ng/ml, the standard deviation was 0.11ng/ml and the coefficient of variation was 11%.

In testing for cross-reactivity, various steroids were tested to determine the concentration required to give a response equivalent to the response obtained with 0.5ng/ml digoxin. The results are reported for the determinations in serum. The following table indicates the results.

TABLE

| Cross-Reactivity | |
|---|---|
| Substance | ng/ml |
| Digoxin | 0.5 |
| Digitoxin | 1.1 |
| Digoxigenin | 0.9 |
| Digitoxigenin | 2.0 |
| Ouabain | ~40.0 |
| Prednisone | 100.0 |
| Spironolactone | >50.0 |
| Cholesterol | >12.0* |
| Cortisone-21-acetate | >20.0 |
| Progesterone | >30.0 |

*aqueous sample

It is evident from the above table that with the exception of the cardiac glycosides and aglycones resembling digoxin and digoxigenin, the assay is highly specific and is readily able to distinguish the desired compounds from other steroids having similar structure. Thus, an accurate determination of the desired compounds can be obtained without concomitant interference from structurally similar steroid compounds.

The digoxin derivative conjugates to enzymes find effective use in the determination of digoxin and digoxigenin. The conjugates are highly specific for the compounds of interest and can determine the compounds of interest at low concentrations. In addition, the enzymes find use in a homgeneous enzyme immunoassay, which does not require a separation step. Thus, by mixing the various reagents and allowing sufficient time for the enzymatic reaction to occur, one can directly read the amount of digoxin or digoxigenin, by comparing the result to a curve prepared from standards having known amounts of digoxin or digoxigenin.

Although the foregoing invention has been described in some detail by way of illustration and example for purposes of clarity of understanding, it will be obvious that certain changes and modifications may be practiced within the scope of the appended claims.

What is claimed is:

1. A conjugate of a cardiac glycoside or aglycone from digitalis to an enzyme wherein both of said cardiac glycoside or aglycone are derived from digitalis and are bonded at other than the active site of said enzyme, wherein said enzyme retains a substantial proportion of the activity of said enzyme prior to conjugation.

2. A cardiac glycoside- or aglycone-bound-enzyme, wherein said cardiac glycoside or aglycone is derived from digitalis of the formula:

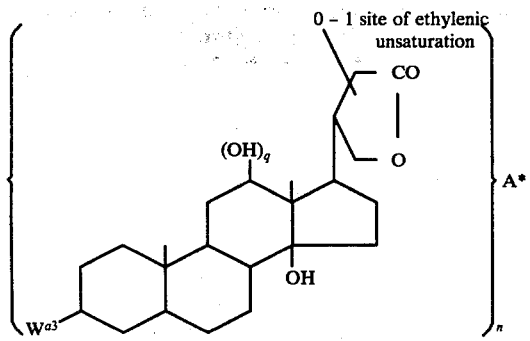

$n$ is on the average in the range of from 1 to 20;
A* is an enzyme; $q$ is 0 or 1; and
$W^{a3}$ is a linking group which is singly or doubly bonded to the annular carbon atom to which $W^{a3}$ is attached.

3. A cardiac glycoside- or aglycone-bound-enzyme according to claim 2, wherein $W^{a3}$ is bonded to said enzyme through amide links or, the nitrogen or sulfur analogs thereof.

4. A cardiac glycoside- or aglycone-bound-enzyme according to claim 3,
wherein $W^{a3}$ is of the formula

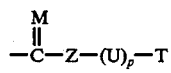

wherein:
T is a single or double bond to the annular carbon atom, being a single bond when bonded to oxygen and a single or double bond when bonded to carbon or nitrogen
$p$ is 0 or 1;
U is amino, being alkylamino of from 1 to 3 carbon atoms when T is a single bond, oxy or aminooxy;
M is chalcogen or imino;
Z is aliphatic hydrocarbylene having up to 1 site of ethylenic unsaturation and of from 1 to 7 carbon atoms.

5. A cardiac glycoside- or aglycone-bound-enzyme according to claim 3, wherein said enzyme is an oxidoreductase.

6. A cardiac glycoside- or aglycone-bound-enzyme according to claim 5, wherein said enzyme is a dehydrogenase.

7. A cardiac glycoside- or aglycone-bound-enzyme according to claim 6, wherein said enzyme is glucose-6-phosphate dehydrogenase.

8. A cardiac glycoside- or aglycone-bound-enzyme according to claim 3, wherein:
$W^{a3}$ is of the formula

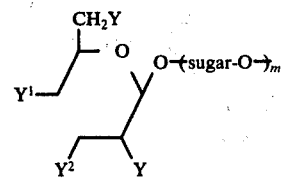

wherein:

$m$ is an integer in the range of 0 to 2;
sugar intends sugars associated with cardiac glycosides;
Y is hydrogen or hydroxyl; and
$Y^1$ and $Y^2$ are single bonds to amino residue of said enzyme or are taken together to provide an iminoalkylene (non-oxocarbonyl) group of from 2 to 8 carbon atoms.

9. A cardiac glycoside- or aglycone-bound-enzyme according to claim 8, wherein said enzyme is an oxidoreductase.

10. A cardiac glycoside- or aglycone-bound-enzyme according to claim 9, wherein said enzyme is a dehydrogenase.

11. A cardiac glycoside- or aglycone-bound-enzyme according to claim 10, wherein said enzyme is glucose-6-phosphate dehydrogenase.

12. A compound of the formula:

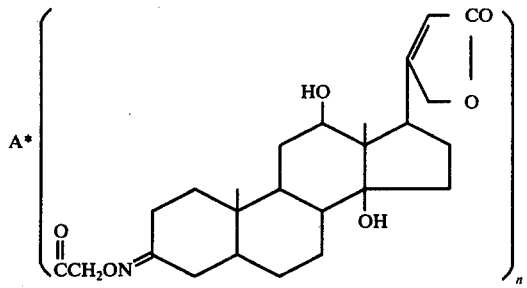

wherein A* is glucose-6-phosphate dehydrogenase and $n$ is on the average in the range of 2 to 10.

13. A compound of the formula:

wherein A* is a glucose-6-phosphate dehydrogenase, $m$ is in the range of 0 to 2, $n$ is on the average in the range of 2 to 10 and sugar intends digitoxose.

* * * * *